(12) United States Patent
Peng et al.

(10) Patent No.: US 7,888,538 B1
(45) Date of Patent: Feb. 15, 2011

(54) CATALYZED OLEFIN INSERTION

(75) Inventors: Sheng Peng, Hockessin, DE (US); Kenneth Gene Moloy, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/612,180

(22) Filed: Nov. 4, 2009

(51) Int. Cl.
*C07C 17/266* (2006.01)
(52) U.S. Cl. .................................... 570/172
(58) Field of Classification Search ............. 570/172
See application file for complete search history.

(56) References Cited

U.S. PATENT DOCUMENTS

| | | | |
|---|---|---|---|
| 3,016,406 A | 1/1962 | Brace et al. |
| 3,226,449 A | 12/1965 | Bianchard et al. |
| 3,933,931 A | 1/1976 | Oda et al. |
| 3,956,412 A | 5/1976 | Knell |
| 3,979,469 A | 9/1976 | Jager |
| 5,585,517 A | 12/1996 | Deisenroth et al. |
| 5,602,228 A | 2/1997 | Wang et al. |
| 5,639,923 A | 6/1997 | Von Werner |
| 5,681,902 A | 10/1997 | May |
| 6,919,490 B2 | 7/2005 | Funakoshi et al. |
| 7,214,815 B2 | 5/2007 | Funakoshi et al. |

FOREIGN PATENT DOCUMENTS

| | | |
|---|---|---|
| CN | 1927787 | 3/2007 |
| CN | 1927788 | 3/2007 |
| CN | 1927791 | 3/2007 |
| GB | 1289191 | 9/1972 |
| GB | 1319898 | 6/1973 |
| GB | 1411137 | 10/1975 |
| JP | 56002054 | 1/1981 |
| JP | 2002316956 | 10/2002 |
| JP | 2004269413 | 9/2004 |
| JP | 58192836 | 1/2010 |
| KR | 2001019202 | 3/2001 |
| KR | 2001019203 | 3/2001 |
| KR | 569245 | 4/2006 |
| KR | 2006115803 | 11/2006 |
| RU | 2144019 | 1/2000 |
| WO | 0236530 | 5/2002 |
| WO | 03091187 | 11/2003 |

OTHER PUBLICATIONS

U.S. Appl. No. 12/612,161, filed Nov. 4, 2009, Peng et al.
Wu et al., Studies on sulfinatodehalogenation: The addition of polyfluoroalkyl iodides to olefins promoted by sodium bisulfite and sodium sulfite, Journal of Fluorine Chemistry, 128, (2007), 84-86, Elsevier B.V.
Lumbierres et al., Addition of perfluorooctyl iodide to alkenes. Catalysis by triphenylphosphane, Tetrahedron, 58, (2002), 4061-4065, Elsevier Science Ltd.
Qui et al., Reaction of Perfluoroalkyl Iodides with Electron-Deficient Olefins under UV irradiation, Journal Organic Chemistry, (1995), 60, 3465-3472, American Chemical Society.
Balague et al., Synthesis of fluorinated telomers. Part 1, Telomerization of vinylidene fluoride with perfluoroalkyl iodides, Journal of Fluorine Chemistry, 70, (1995), 215-223, Elsevier Science S.A.
Uneyama et al., Palladium-Catalyzed Coupling Reactions of Trifluoroaoetimidoyl Iodides with Olefins and 1-Alkynes, Tetrahedron Letters, vol. 32, No, 11, pp. 1459-1462, 1991, Pergamon Press plc.
Chen et al., Copper-Induced Telomerization of Tetrafluoroethylene with Fluoroalkyl Iodides, Journal of Fluorine Chemistry, 36, (1987), 483-489, Elsevier Sequoia, The Netherlands.
Heinze et al., Palladium Catalyzed Coupling of F-Vinyl Zinc Reagents with Aryl Iodides. An Improved Synthesis of Alpha, Beta, Beta-Trifluorostyrenes and the Stereospecific Preparation of 1-Phenyl-F-Propenes, Journal of Fluorine Chemistry, 31, (1986), 115-119, Elsevier Sequoia, The Netherlands.
Von Werner, Reactions of perfluoroalkyl iodides with CC-multiple bonds induced by transition metal centers, Journal of Fluorine Chemistry, 28, (1985), 229-233, Elsevier Sequoia, The Netherlands.
Abstract of Chen et al., Fluoroalkylation and fluoroalkoxylation. 9. Platinum (0)-catalyzed addition reactions of fluoroalkyl iodides with olefins, Youji Huaxue, (1986), (1), 41-43, Shanghai Institute Organic Chemical, Academy Sin., Shanghai, People's Republic of China.
Abstract of Chen et al., Fluoroalkylation and fluoroalkoxylation. 9. Platinum (0)-catalyzed addition reactions of fluoroalkyl iodides with olefins, Huaxue Xuebao, (1985), 43(11), 1118-1120, Shanghai Institute Organic Chemical, Academy Sin., Shanghai, People's Republic of China.

*Primary Examiner*—Jafar Parsa
(74) *Attorney, Agent, or Firm*—Nancy S. Mayer

(57) ABSTRACT

A process for the insertion of a partially fluorinated olefin into a fluorinated iodide in the presence of a nickel catalyst at a temperature of a maximum of 150° C. with an initial rate of 0.01 mole/hour without loss of selectivity is disclosed, as well as use of the process for insertion of a perfluorinated olefin with an initial rate of 0.04 mole/hour.

10 Claims, No Drawings

CATALYZED OLEFIN INSERTION

FIELD OF THE INVENTION

This invention relates to a process for the insertion of an olefin into a fluorinated iodide in the presence of a nickel catalyst.

BACKGROUND OF THE INVENTION

Fluorine-containing alkyl iodides have a broad range of industrial applications. Fluorine-containing alkyl iodides can be prepared by thermal and redox-induced telomerizations of olefins with linear or branched perfluoroalkyl iodides. The thermal telomerizations are typically conducted at temperatures greater than about 200° C. at high pressures and usually lead to mixtures of homologue telomers in the product requiring sequential separation. Expensive specialized equipment is required to conduct the telomerization at such high temperatures and pressures. If lower temperatures are employed, then the conversion rate drops to unacceptable levels. Telomerization reaction of addition of an olefinic compound to perfluoroalkyl iodides in the presence of a free radical initiator solution also leads to mixtures of telomere products and sequential separation of the products is required.

It has been reported by Qing-Yun Chen, et al., in Journal of Fluorine Chemistry 36 (1987) 483-389, that polyfluoroalkyl iodides can be prepared at a lower temperature of about 80-100° C. by the telomerization reaction of perfluoroalkyl iodides with a fluorinated olefinic compound such as tetrafluoroethylene, in the presence of a copper catalyst. However, it has been discovered that copper catalyst does not work efficiently in some olefin addition or insertion reactions, especially in such reactions wherein the olefinic compound is vinylidene fluoride.

In connection with ethylene addition reactions, processes employing ruthenium/activated carbon (Ru/C), platinum/activated carbon (Pt/C), silver/alumina (Ag/Al$_2$O$_3$), and like noble metals as catalysts are reported by Konrad von Werner in Journal of Fluorine Chemistry 28 (1985); 229-233. However, use of the noble metals has the disadvantage that they are expensive and thus result in high production costs. Further some such catalysts are not readily available commercially and are difficult or toxic to prepare.

It is desirable to have a process for the insertion of an olefin into a fluoroalkyliodide which can be conducted at a lower temperature than the traditional thermal processes using a readily available inexpensive catalyst at an acceptable conversion rate with good selectivity for particular homologue telomer products. The present invention provides such a process for the preparation of a fluoroalkyl iodide by the insertion of an olefin into the carbon-iodine bond of a fluoroalkyl iodide in the presence of a nickel derivative catalyst. The process of the invention is operated at a temperature from about 60° to 150° C.

BRIEF SUMMARY OF THE INVENTION

The present invention comprises a process for the preparation of a compound of Formula (I)

$$R_f[C(X_1X_2)C(Y_1Y_2)]_nI \tag{I}$$

wherein
each $X_1$, $X_2$, $Y_1$, and $Y_2$ is independently fluorine, hydrogen, fluoroalkyl, or fluoroalkoxy;
n is 1, 2, or 3; and $R_f$ is a perfluorinated or partially fluorinated carbon chain optionally interrupted with catenary oxygen or catenary sulfur;

comprising contacting, at a temperature of a maximum of 150° C. and at an initial rate of a minimum of about 0.01 mole/hour, a partially fluorinated olefin with a fluoroalkyl iodide $R_fI$ wherein $R_f$ is defined as above, in the presence of a catalyst, wherein said catalyst is i) Ni(Z)$_m$ wherein each Z is independently PR$_3$; m is 2 to 4; R is phenyl, alkyl substituted phenyl, or C$_r$H$_{2r+1}$; and r is 1 to 10; or ii) a mixture of Ni and Z wherein Z is as defined above, to yield a compound of Formula (I) with a selectivity for n is 1 of at least 65%.

The present invention further comprises a process for the preparation of a compound of Formula (I)

$$R_f[C(X_1X_2)C(Y_1Y_2)]_nI \tag{I}$$

wherein
each $X_1$, $X_2$, $Y_1$, and $Y_2$ is independently fluorine, fluoroalkyl, or fluoroalkoxy;
n is 1, 2, or 3; and
$R_f$ is a perfluorinated or partially fluorinated carbon chain optionally interrupted with catenary oxygen or catenary sulfur;

comprising contacting, at a temperature of a maximum of 150° C. and at an initial rate of a minimum of 0.04 mole/hour, an olefin selected from the group consisting of tetrafluoroethylene, hexafluoropropylene, and perfluorinated vinylether with a fluoroalkyl iodide $R_fI$ wherein $R_f$ is defined as above, in the presence of a catalyst, wherein said catalyst is (i) Ni(Z)$_m$ wherein each Z is independently PR$_3$; m is 2 to 4; R is phenyl, alkyl substituted phenyl, or C$_r$H$_{2r+1}$; and r is 1 to 10; or ii) a mixture of Ni and Z wherein Z is as defined above, to yield a compound of Formula (I) with a selectivity for n is 1 of at least 45%.

DETAILED DESCRIPTION OF THE INVENTION

The present invention provides a process for insertion of an olefin into a fluoroalkyl iodide in the presence of a nickel catalyst at low temperature while maintaining excellent conversion rate and selectivity. In particular, the present invention comprises a process for the preparation of a compound of Formula (I)

$$R_f[C(X_1X_2)C(Y_1Y_2)]_nI \tag{I}$$

wherein
each $X_1$, $X_2$, $Y_1$, and $Y_2$ is independently fluorine, hydrogen, fluoroalkyl, or fluoroalkoxy;
n is 1, 2, or 3; and
$R_f$ is a perfluorinated or partially fluorinated carbon chain optionally interrupted with catenary oxygen or catenary sulfur by the insertion of an olefin having structure of $$C(X_1X_2)=C(Y_1Y_2) \tag{II}$$

wherein each $X_1$, $X_2$, $Y_1$ and $Y_2$ are defined as above in Formula (I), into the carbon-iodine bond of a fluoroalkyl iodide $R_fI$ in the presence of catalyst, wherein said catalyst is (i) Ni(Z)$_m$ wherein each Z is independently PR$_3$; m is 2 to 4; R is phenyl, alkyl substituted phenyl, or C$_r$H$_{2r+1}$; and r is 1 to 10; or iii) a mixture of Ni and Z wherein Z is as defined above, to yield a compound of Formula (I) with a selectivity for n is 1 of at least 65%.

One of the advantages of the process of this invention is to provide a high $R_fI$ conversion to telomer products at low temperature. The term "initial rate" is used herein to mean the calculated initial reaction rate obtained by measuring pressure and time during the reaction, graphing pressure versus time, and then measuring the slope of the linear portion of the resulting curve at a short time (low conversion) of 3 hours or less. In accordance with conventional chemical reaction kinetics, the speed of a reaction is the rate at which the concentrations of reactants and products change. The rate of change in the concentration corresponds with the slope of the concentration-time plot. Each species in the reaction has its own rate of change in concentration. The reactants have a negative slope, because they are being consumed in the reaction. Products have a positive slope, because they are being formed in the reaction. Thus one skilled in the art can easily calculate the initial rate of reaction for a particular chemical reaction. Furthermore, one skilled in the art can easily compare the activities of, for instance, different catalysts by comparing the initial rate of reaction for different catalysts under otherwise identical reaction conditions, e.g., temperature, pressure, and reactant concentrations.

In the process of the present invention the compound of Formula (I) is prepared using an olefin compound at an initial rate of a minimum of 0.01 mole/hour. At this rate an acceptable conversion of 60% or higher, up to about 90% to about 100%, is achievable within a maximum of 12 hours of reaction time. Higher initial rates, such as 0.02 mole/hour, 0.04 mole/hour, or 0.08 mole/hour, can be employed.

Another advantage of the process of the present invention is enabling the efficient production of fluoroalkyl iodides without loss of selectivity compared to conventional thermal processes conducted at higher temperatures. Since most prior art processes yield a mixture of telomer products wherein in Formula (I) subscript n is 1, 2 or 3, sequential separation processes are required. The conversion rate is inversely proportional to the selectivity, so maximizing one reduces the other. The process of the present invention achieves acceptable conversion of about 60%, preferably about 70%, 75%, 85%, or higher as noted above, by use of an initial rate of a minimum of 0.01 mole/hour at a lower temperature of about 150° C., while maintaining selectivity comparable to the prior art higher temperature processes conducted at greater than 200° C. Generally the selectivity for compounds of Formula (I) wherein n is 1 is a minimum of about 65%, preferably a minimum of about 75%, and more preferably a minimum of about 80%. Selectivity for n is 1 of about 90% to about 95% is achievable using the process of the present invention. For example, vinylidene fluoride (VDF) can be inserted to produce the first insertion product which is also called monoadduct (n=1 in Formula (I)) at from about 67% to about 100%. Furthermore, the process of the present invention when used in the vinylidene fluoride (VDF) insertion reaction, yields a total amount of the first insertion product (monoadduct, n=1) and the second insertion product (diadduct, n=2) of from about 95% to about 100%.

Fluoroalkyl iodides, $R_fI$, suitable for use in the present invention are iodides wherein $R_f$ is a perfluorinated or partially fluorinated hydrocarbon chain, optionally interrupted with a catenary oxygen or catenary sulfur group. Preferred $R_f$ contains 1 to 6 continuous fluorinated carbons. More preferred $R_f$ contains 1 to 4 continuous fluorinated carbons. Each optional oxygen or sulfur is bonded to at least two carbons. No oxygen or sulfur is bonded to second oxygen or sulfur, or to each other. Examples of suitable iodides include $C_6F_{13}I$, $C_4F_9I$, $C_2F_5I$, $C_6F_{13}CH_2CF_2I$, $C_4F_9CH_2CF_2I$, $C_3F_7OC_2F_4I$, $C_2F_5OC_2F_4I$, and $CF_3OC_2F_4I$.

Olefins suitable for the use in the present invention are represented by the structure of Formula (II)

$$C(X_1X_2)=C(Y_1Y_2) \qquad (II)$$

wherein each $X_1$, $X_2$, $Y_1$, and $Y_2$ are independently fluorine, hydrogen, fluoroalkyl, or fluoroalkoxy. The olefins suitable for the use in the present invention can be characterized in two groups as follows 1) partially fluorinated olefins and 2) perfluorinated olefins. Partially fluorinated olefins are exemplified by trifluoromethyl propene, vinyl fluoride, partially fluorinated vinylether, vinylidene fluoride, and the like. Preferred olefins are vinyl fluoride and vinylidene fluoride. Perfluorinated olefins are exemplified by tetrafluoroethylene, hexafluoropropylene, and perfluorinated vinylether. The conversion and selectivity for use of the perfluorinated olefins as reactants are generally lower, and thus require a higher minimum initial rate as discussed hereinafter. When perfluorinated olefins are employed each of $X_1$, $X_2$, $Y_1$, and $Y_2$ in Formula (I) and (II) are not hydrogen, but are otherwise as defined above.

The process of the present invention is also suitable for use with other olefins. Such other olefins include other halogenated olefins, such as vinyl chloride, vinylidene chloride, trichloromethyl propene, or chlorinated vinylether. Such other olefins also include hydrocarbon olefins such as alkenes, in particular ethylene, propylene and similar alkenes.

The process of the present invention uses a nickel catalyst which is either 1) a compound of the type $Ni(Z)_m$ wherein each Z is independently $PR_3$; m is 2 to 4; R is phenyl, alkyl substituted phenyl, or $C_rH_{2r+1}$; and r is 1 to 10; or 2) a mixture of Ni metal and Z wherein Z is as defined above. Preferred catalysts for use herein are a mixture of nickel and triphenylphosphine, or nickel and tributylphosphine. Preferably the nickel in the catalyst is powdered having a particle diameter of about 0.03 mm, but more coarse nickel, such a nickel mesh of about 0.14 diameter, or nickel shot of about 3 to about 25 mm in diameter, can also be employed in the process of the present invention. The nickel catalyst is readily available commercially and is inexpensive. For example, nickel powder is commercially available from Inco Special Products, Mississauga, Ontario, Canada.

The temperature employed in the process of the present invention is from about 60° C. to about 150° C. Preferably the temperature is from about 80° C. to about 130° C., and more preferably from about 90° C. to about 120° C. Use of temperatures within this range do not require the specialized equipment needed by the high temperature prior art processes.

The fluoroalkyl iodide is contacted with the olefin in the presence of the catalyst. The mole ratio of iodide to olefin can range from about 1:2 to about 2:1. Preferably the ratio is from about 1:1.8 to about 1.5:1, and most preferably the ratio is from about 1:1.5 to about 1:1. Typically the reaction is conducted under pressure in an autoclave or equivalent apparatus in the range of from 0.3 psi to about 400 psi (2068 Pa to 2,758,000 Pa). The preferred pressure range is from about 0.3 psi to about 300 psi (2068 Pa to 2,068,599 Pa) and the most preferred range is from about 0.3 psi to about 200 psi (2068 Pa to 1,379,000 Pa). The reaction is permitted to continue for a minimum of about 3 hours. Longer times, such as 6 or 9 hours, can be employed if desired to maximize conversion, but can then potentially result in a loss of selectivity. A maximum of 12 hours can be employed.

The present invention further comprises a process for the preparation of a compound of Formula (I)

$$R_f[C(X_1X_2)C(Y_1Y_2)]_nI \qquad (I)$$

wherein each $X_1$, $X_2$, $Y_1$, and $Y_2$ is independently fluorine, fluoroalkyl, or fluoroalkoxy;

n is 1, 2, or 3; and $R_f$ is a perfluorinated or partially fluorinated carbon chain optionally interrupted with catenary oxygen or catenary sulfur;

comprising contacting, at a temperature of a maximum of 150° C. and at an initial rate of a minimum of 0.04 mole/hour, an olefin selected from the group consisting of tetrafluoroethylene, hexafluoropropylene, and perfluorinated vinylether, with a fluoroalkyl iodide $R_fI$ wherein $R_f$ is defined as above, in the presence of a catalyst, wherein said catalyst is (i) $Ni(Z)_m$ wherein each Z is independently $PR_3$; m is 2 to 4; R is phenyl, alkyl substituted phenyl, or $C_rH_{2r+1}$; and r is 1 to 10; or iv) a mixture of Ni and Z wherein Z is as defined above, to yield a compound of Formula (I) with a selectivity for n is 1 of at least 45%.

For tetrafluoroethylene, hexafluoropropylene, and perfluorinated vinylether the selectivity for the monoadduct is lower than for the partially fluorinated olefins using the process of the present invention, but is still comparable to the prior art higher temperature processes. A selectivity for n is 1 of a minimum of 45% is achievable, preferably a selectivity of a minimum of about 50%. An initial rate higher than that for partially fluorinated olefins is used to obtain acceptable conversion without loss of selectivity compared to conventional thermal processes run at higher temperatures. An initial rate of a minimum of 0.04 moles/hour is employed. Higher initial rates of a minimum of about 0.06 moles/hour, or 0.08 moles/hour can also be employed. Suitable catalysts and fluoroalkyl iodides for use with the perfluorinated olefins are as described above for partially fluorinated olefins. Suitable reaction conditions, such as temperature, ratio of reactants, reaction time for the insertion of tetrafluoroethylene, hexafluoropropylene, or perfluorinated vinylether into a perfluoroalkyl iodide are as described above for the partially fluorinated olefin insertion.

The present invention is useful to prepare compounds of Formula (I) at a low temperature with excellent conversion without loss of selectivity compared to conventional prior art thermal processes. The catalyst employed is readily available and inexpensive, thus rendering the process more economical. The lower temperatures employed do not require specialized expensive equipment. The compounds of Formula (I) have a wide variety of industrial applications including, for example, as surfactants, in pharmaceutical end uses, and as functional polymers.

Materials

The following materials were used in the Examples herein.

Tetrafluoroethylene is available from E. I. du Pont de Nemours and Company, Wilmington, Del.

Nickel powder (less than 0.03 mm) is available from Inco Special Products, Mississauga, Ontario, Canada. Nickel shot (3-25 mm) and 100 mesh nickel (0.14 mm) are available from Alfa-Aesar, Ward Hill, Mass.

Other reagents are readily commercially available, for example, from Sigma-Aldrich Chemical Co., Milwaukee, Wis.

EXAMPLES

Example 1

Vinylidene fluoride (VDF) (25.7 g) was introduced to an autoclave charged with $C_4F_9I$ (100 g) and Ni (0.34 g) and $PPh_3$ (0.76 g), and the reactor was heated at 150° C. for 3 hours. The pressure was monitored with a gauge and the initial reaction rate was calculated by plotting the pressure versus time, and then measuring the slope of the linear portion of the curve at short time (low conversion) of 3 hours or less. The reaction mixture was subjected to gas chromatography for products analysis, and results are shown in Table 1.

Examples 2-3

The above procedure and reactants of Example 1 were also applied to Examples 2 and 3 using the catalyst as indicated in Table 1. The initial reaction rate was determined by the method described in Example 1. The reaction mixture was subjected to gas chromatography for products analysis, and results are shown in Table 1.

Comparative Example 1A

Vinylidene fluoride (25.7 g) was introduced to an autoclave charged with $C_4F_9I$ (100 g), and the reactor was heated at 210° C. for 3 hours. No catalyst was employed. The initial reaction rate was determined by the method described in Example 1. The reaction mixture was subjected to gas chromatography for products analysis, and results are shown in Table 1.

Comparative Examples 1B-1C

The above procedure and reactants of Comparative Example 1A were employed for Comparative Examples 1B and 1C at a temperature of 180° C. and 150° C. respectively. The reaction was conducted for 12 hours. The initial reaction rate was determined by the method described in Example 1. The reaction mixture was subjected to gas chromatography for products analysis, and results are shown in Table 1.

Comparative Example 2A

Vinylidene fluoride (25.7 g) was introduced to an autoclave charged with $C_4F_9I$ (100 g) and Cu (0860T ⅛, 0.64 g), and the reactor was heated at 180° C. for 12 h. The initial reaction rate was determined by the method described in Example 1. The reaction mixture was subjected to gas chromatography for products analysis, and results are shown in Table 1.

Comparative Example 2B-2D

The above procedure and reactants of Comparative Example 2A were repeated as Comparative Examples 2B to 2D at a temperature of 150° C. using the following catalysts: Ni, Pd(PPh₃), and (Ph₃P)₂Ni(CO) as indicated in Table 1. The initial reaction rate was determined by the method described in Example 1. However, in the case of $(PPh_3)_2Ni(CO)_2$ gas uptake was noted as the autoclave was being heated but upon reaching the 150° C. target temperature gas uptake had ceased, indicating that the catalyst was no longer functioning due to decomposition. The reaction mixture was subjected to gas chromatography for products analysis, and results are shown in Table 1.

TABLE 1

Vinylidene Fluoride insertion into $C_4F_9I$

| | Catalyst | T (° C.) | t (hour) | Conversion (%) | Initial Rate mole/hour | Selectivity (%) (1VDF:2VDF:3VDF) (n = 1:n = 2:n = 3) Formula (I)) |
|---|---|---|---|---|---|---|
| Examples | | | | | | |
| 1* | Ni/PPh$_3$ | 150 | 3 | 70 | 0.04 | 89:10:1 |
| 2* | Ni/PPh$_3$ | 150 | 12 | 93 | 0.04 | 75:22:3 |
| 3* | Ni/PBu$_3$ | 150 | 3 | 96 | 0.08 | 67:28:5 |
| 4 | Ni (100 mesh)/PPh$_3$ | 150 | 3 | 40 | 0.02 | 96:4:0 |
| 5 | Ni (shot)/PPh$_3$ | 150 | 3 | 35 | 0.01 | 96:4:0 |
| Comparative Examples | | | | | | |
| 1A | None | 210 | 3 | 88.5 | 0.08 | 66:28:6 |
| 1B | None | 180 | 12 | 80 | 0.04 | 74:22:4 |
| 1C | None | 150 | 12 | 30.5 | 0.004 | 84:14:2 |
| 2A | Cu | 180 | 12 | 80 | 0.04 | 73:23:4 |
| 2B* | Ni | 150 | 3 | 6 | 0.002 | 91:9:0 |
| 2C | Pd(PPh$_3$)$_4$ | 150 | 3 | 35 | 0.002 | 96:4:0 |
| 2D | (Ph$_3$P)$_2$Ni(CO)$_2$ | 150 | 3 | 85 | | 85:14:1 |

*Ni powder was used

The above results in Table 1 have shown that the process of the present invention using the Ni derivative catalysts in Example 1, 2 and 3 provided comparable conversions and initial rates to the uncatalyzed reaction at higher temperature of Comparative Examples 1A and 1B. At the same temperature (150° C.), Examples 1 to 3 of the invention demonstrated superior conversion and initial rates compared to Comparative Example 1C. Examples 1 to 3 also showed equal or better conversions and selectivity to the catalyzed reactions of Comparative Examples 2A to 2D. Examples 4 and 5 demonstrated that the present invention is not only limited to nickel powder as used in Examples 1 and 3, but that coarse metal can be used in combination with phosphorus ligand and still achieve better conversion than the uncatalyzed reaction of Comparative Example 1C at the same temperature, or better conversion than using nickel alone in Comparative Example 2B at the same temperature.

Comparative Examples 1A to 1C demonstrated that lowering the temperature of the conventional thermal process resulted in a decrease in conversion with unacceptable initial rates at 150° C. Comparative Examples 2A and 2B demonstrated that unpromoted copper and nickel do not improve upon the rate over the thermal process of Comparative Examples 1A and 1B. Comparative Examples 2C and 2D demonstrated that these prior art catalysts were inferior to the catalysts described in this invention. For instance, Comparative Example 2C showed that prior art catalyst Pd(PPh$_3$)$_4$, derived from an expensive precious metal, gave slower rates than the much less expensive nickel catalysts in the Examples of the invention. Prior art catalyst (PPh$_3$)$_2$Ni(CO)$_2$, in addition to being toxic and synthesized from toxic chemicals, decomposed before the reaction was complete, which is unacceptable for commercial application.

Examples 6 to 8

The above procedure of Example 1 was employed, except that tetrafluoroethylene was used as the olefin. The initial reaction rate was determined by the method described in Example 1. The reaction mixture was subjected to gas chromatography for products analysis, and results are shown in Table 2.

Comparative Example 3A

The above procedure of Comparative Example 1A was employed, except that tetrafluoroethylene was used as the olefin, and the reactor was heated at 230° C. for 3 hours. The reaction was substantially complete by the time the reactor reached this high temperature and the initial rate was not measured. The reaction mixture was subjected to gas chromatography for products analysis, and results are shown in Table 2.

Comparative Example 3B

The above procedure of Comparative Example 3A was also applied to Comparative Example 3B at 150° C. The initial reaction rate was determined by the method described in Example 1. The reaction mixture was subjected to gas chromatography for products analysis, and results are shown in Table 2.

Comparative Example 3C

The above procedure of Examples 6 and 7 was also applied to Comparative Example 3C using (PPh$_3$)$_2$Ni(CO)$_2$ as catalyst at 150° C. Gas uptake was noted as the autoclave was being heated but upon reaching the 150° C. target temperature gas uptake had ceased, indicating that the catalyst was no longer functioning due to decomposition. The reaction mixture was subjected to gas chromatography for products analysis, and results are shown in Table 2.

TABLE 2

Tetrafluoroethylene insertion into $C_4F_9I$

| | Catalyst | T (°C.) | t (hour) | Conversion (%) | Initial Rate mole/hour | Selectivity (%) (1TEF:2TEF:3TEF and above) |
|---|---|---|---|---|---|---|
| Example | | | | | | |
| 6* | Ni/PPh3 | 150 | 3 | 37 | 0.04 | 49:19:31 |
| 7* | Ni/PBu3 | 150 | 3 | 49 | 0.08 | 51:22:27 |
| Comparative Example | | | | | | |
| 3A | None | 230 | 3 | 57.0 | | 43:25:32 |
| 3B | None | 150 | 3 | 30 | 0.03 | 42:26:32 |
| 3C | $(Ph_3P)_2Ni(CO)_2$ | 150 | 3 | 59.0 | | 54:25:21 |

*Ni powder was used in the catalyst.

The above results in Table 2 have shown that the process of the present invention using the Ni derivative catalysts in Examples 6 and 7 provided comparable conversions and selectivity in tetrafluoroethylene insertion reaction at lower temperature compared to the results from Comparative Example 3A in which the reaction was carried out at higher temperature without catalyst. Examples 6 and 7 showed better conversion and selectivity than the results from Comparative Example 3B in which the reaction was carried out at the same temperature without the catalyst. Examples 6 and 7 showed good rate, conversion, and selectivity compared to prior art catalyst $(PPh_3)_2Ni(CO)_2$ in Comparative Example 3C. However, as noted previously this prior art catalyst is toxic, and showed poor stability under the reaction conditions by decomposing.

What is claimed is:

1. A process for the preparation of a compound of Formula (I)

$$R_f[C(X_1X_2)C(Y_1Y_2)]_nI \qquad (I)$$

wherein
each $X_1$, $X_2$, $Y_1$, and $Y_2$ is independently fluorine, hydrogen, fluoroalkyl, or fluoroalkoxy;
n is 1, 2, or 3; and
$R_f$ is a perfluorinated or partially fluorinated carbon chain optionally interrupted with catenary oxygen or catenary sulfur;
comprising contacting, at a temperature of a maximum of 150° C. and at an initial rate of a minimum of 0.01 mole/hour, a partially fluorinated olefin with a fluoroalkyl iodide $R_fI$ wherein $R_f$ is defined as above, in the presence of a catalyst, wherein said catalyst is
iii) $Ni(Z)_m$ wherein each Z is independently $PR_3$; m is 2 to 4; R is phenyl, alkyl substituted phenyl, or $C_rH_{2r+1}$; and r is 1 to 10; or
iv) a mixture of Ni and Z wherein Z is as defined above, to yield a compound of Formula (I) with a selectivity for n is 1 of at least 65%.

2. The process of claim 1, wherein $R_f$ contains 1 to 6 continuous fluorinated carbons.

3. The process of claim 1, wherein $R_f$ contains 1 to 4 continuous fluorinated carbons.

4. The process of claim 1 wherein each of $Y_1$ and $Y_2$ is fluorine.

5. The process of claim 1 wherein the catalyst is a mixture of nickel and triphenylphosphine or a mixture of nickel and tributylphosphine.

6. The process of claim 1 wherein the olefin is trifluoromethyl propene, vinyl fluoride, fluorinated vinylether, or vinylidene fluoride.

7. The process of claim 1 wherein the temperature is from about 60° C. to about 150° C.

8. The process of claim 1 wherein the ratio of fluoroalkyl iodide to olefin is from about 1:2 to about 2:1.

9. The process of claim 1 wherein the initial rate is a minimum of 0.02 mole/hour.

10. The process of claim 1 wherein the selectivity for n is 1 is a minimum of about 75%.

* * * * *